United States Patent [19]

Machida et al.

[11] Patent Number: 4,977,780
[45] Date of Patent: Dec. 18, 1990

[54] ULTRASONIC PROBE DEVICE

[75] Inventors: Kaoru Machida; Yusichi Kikuchi; Masayuki Takano; Noriyoshi Kobayashi, all of Otawara, Japan

[73] Assignee: Kabushiki Kaisha Toshiba, Kanagawa, Japan

[21] Appl. No.: 500,115

[22] Filed: Mar. 27, 1990

Related U.S. Application Data

[63] Continuation of Ser. No. 325,049, Mar. 16, 1989, abandoned, which is a continuation of Ser. No. 116,247, Nov. 3, 1987, abandoned.

[30] Foreign Application Priority Data

Nov. 6, 1986 [JP] Japan .............................. 61-264774
Nov. 25, 1986 [JP] Japan .............................. 61-280296

[51] Int. Cl.$^5$ ............................................. G01N 29/04
[52] U.S. Cl. .................................. 73/644; 128/662.03
[58] Field of Search ................ 73/628, 629, 632, 644; 128/662.03–662.06, 663.01, 642, 644

[56] References Cited

U.S. PATENT DOCUMENTS

| 3,175,106 | 3/1965 | Sansom et al. | 73/644 |
|---|---|---|---|
| 3,213,676 | 10/1965 | Makous | 73/644 |
| 4,020,679 | 5/1977 | Barry | 73/629 |
| 4,127,872 | 11/1978 | Hassler | 128/663 |
| 4,265,126 | 5/1981 | Papadofrangakis et al. | 128/663 |
| 4,294,119 | 10/1981 | Soldner | 128/660 |
| 4,327,739 | 5/1982 | Chmiel et al. | 128/663 |
| 4,353,258 | 10/1982 | Hunter | 73/644 |
| 4,407,293 | 10/1983 | Suarez, Jr. et al. | 73/620 |
| 4,458,534 | 7/1984 | Kising | 73/625 |
| 4,556,066 | 12/1985 | Semrow | 128/660 |
| 4,722,346 | 2/1988 | Chen | 128/662.03 |

Primary Examiner—John Chapman
Assistant Examiner—Rose M. Finley
Attorney, Agent, or Firm—Finnegan, Henderson, Farabow, Garrett, and Dunner

[57] ABSTRACT

An ultrasonic probe device includes an ultrasonic probe for transmitting ultrasonic waves toward and receiving ultrasonic echoes from a target region in a body under examination, and an ultrasonic coupler for being interposed between the ultrasonic probe and the surface of the body. The ultrasonic probe device can accurately detect Doppler information on the central area of the target region.

6 Claims, 9 Drawing Sheets

ULTRASONIC PROBE DEVICE

This application is a continuation, of application Ser. No. 07/325,049, filed Mar. 16, 1989, now abandoned, which is a continuation of application Ser. No. 07/116,247, filed Nov. 3, 1987, now abandoned.

BACKGROUND OF THE INVENTION

The present invention relates to an ultrasonic probe device having an ultrasonic probe for transmitting ultrasonic waves toward and receiving ultrasonic echoes from a target region in a body under examination, and an ultrasonic coupler for being interposed between the ultrasonic probe and the surface of the body.

Figure 12:
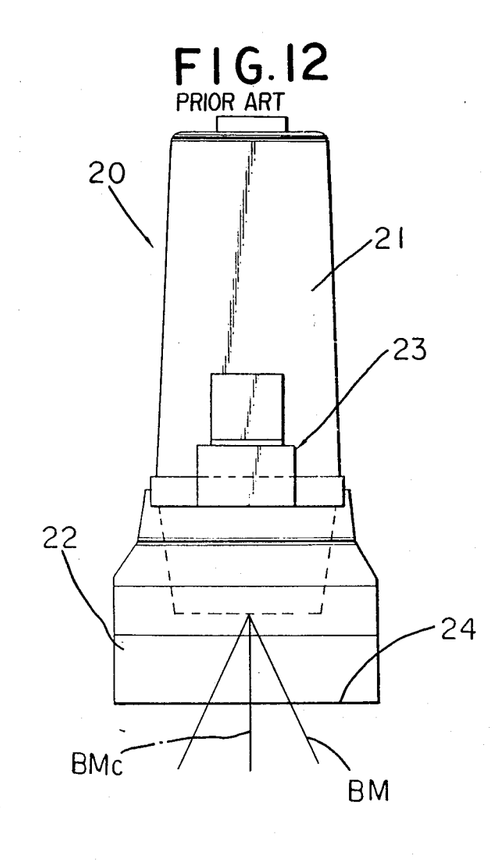
FIG. 12 is a front elevational view of a conventional ultrasonic probe device.
Figure 13:
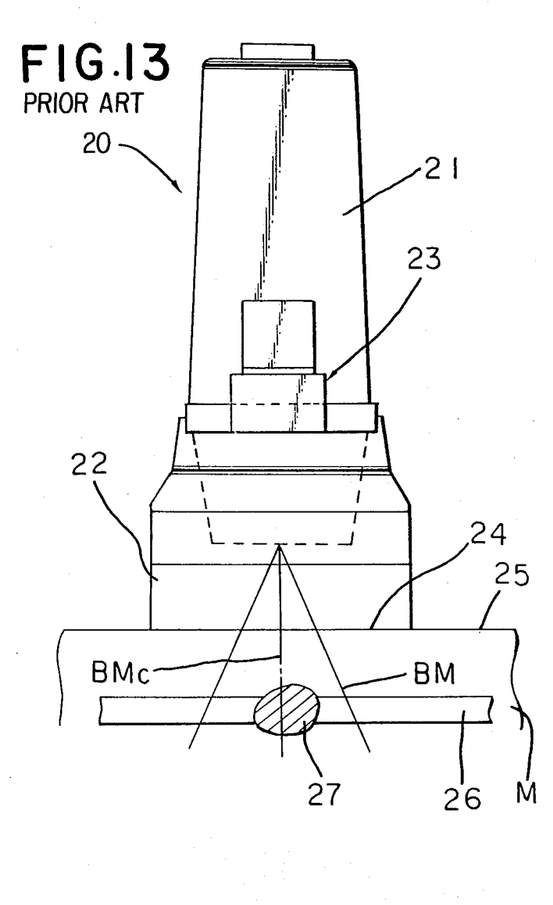
FIG. 13 is a front elevational view showing the manner in which the conventional ultrasonic probe device is used.

One conventional ultrasonic probe device comprising an ultrasonic probe and an ultrasonic coupler is illustrated in FIGS. 12 and 13 of the accompanying drawings.

The ultrasonic probe device, generally denoted at 20 in FIG. 12, includes an ultrasonic probe 21 for transmitting ultrasonic waves and receiving ultrasonic echoes, and an ultrasonic coupler 22 having a mount 23 by which the ultrasonic coupler 22 is mounted on the ultrasonic probe 21 and a surface 24 for contacting the surface 25 (FIG. 13) of a body M being examined, the ultrasonic coupler 22 containing an acoustic medium such as water. The ultrasonic coupler 22 is in the form of a water bag or a soft container housing a soft colloidal material or the like. Therefore, the ultrasonic coupler 22 is flexible enough to allow the contacting surface 24 to be of a flat, symmetrical shape with respect to a central line BMc in the plane in which an ultrasonic beam BM is scanned, or to be freely deformed.

The ultrasonic probe 20 may be used to obtain Doppler information (FFT Doppler information, two-dimensional color Doppler information) on a peripheral blood vessel 26 such as a carotid artery running substantially parallel to the surface 25 of the body M. However, most important Doppler information on a central area of the ultrasonic beam BM, i.e., a central area of a target region 27, may not be accurately obtained or may not entirely be measured. This results from the principles of the Doppler effect. More specifically, the relationship between a Doppler shift frequency fd and a blood speed V is expressed by:

$$fd = \frac{2V\cos\alpha}{C} f$$

where $\alpha$ is the angle formed between the ultrasonic beam and the blood stream, f is the driving frequency, and C is the speed of sound in the body being examined. Since the angle $\alpha$ between the blood stream and the ultrasonic beam BM is 90° in the target region 27, fd=0 and the speed of the blood flow cannot be measured.

Another cause of the trouble is that the flat symmetrical contacting surface 24 of the ultrasonic coupler 22 causes multiple reflections of the ultrasonic echo.

As described above, the conventional ultrasonic probe device cannot obtain accurate Doppler information on the central area of the target region to be measured.

SUMMARY OF THE INVENTION

It is an object of the present invention to provide an ultrasonic probe device capable of accurately detecting Doppler information on the central area of a target region.

To achieve the above object, there is provided an ultrasonic probe device comprising an ultrasonic probe for transmitting ultrasonic waves toward and receiving ultrasonic echoes from a target region in a body under examination, and an ultrasonic coupler for being interposed between the ultrasonic probe and the surface of the body, the ultrasonic coupler having a surface for contacting the surface of the body, the surface being inclined to a central axis of an ultrasonic beam emitted from the ultrasonic probe.

Since the contacting surface of the ultrasonic coupler is inclined to the central axis of the ultrasonic beam, the ultrasonic beam at its central axis is applied at an angle to the target region of the body being examined. Therefore, the angle $\alpha$ based on the Doppler effect is not 90°, and a Doppler shift frequency fd can be determined.

According to the present invention, there is also provided an ultrasonic probe device comprising an ultrasonic probe for transmitting ultrasonic waves toward and receiving ultrasonic echoes from a target region in a body under examination, and an ultrasonic coupler for being interposed between the ultrasonic probe and the surface of the body, the ultrasonic probe having a vibrator array inclined to the central axis of the ultrasonic probe.

Since the vibration array of the ultrasonic probe is inclined to the central axis of the ultrasonic probe, the ultrasonic beam is applied at an angle corresponding to the angle of inclination of the vibration array to the target region of the body being examined. Therefore, the angle $\alpha$ based on the Doppler effect is not 90°, and a Doppler shift frequency fd can be determined.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
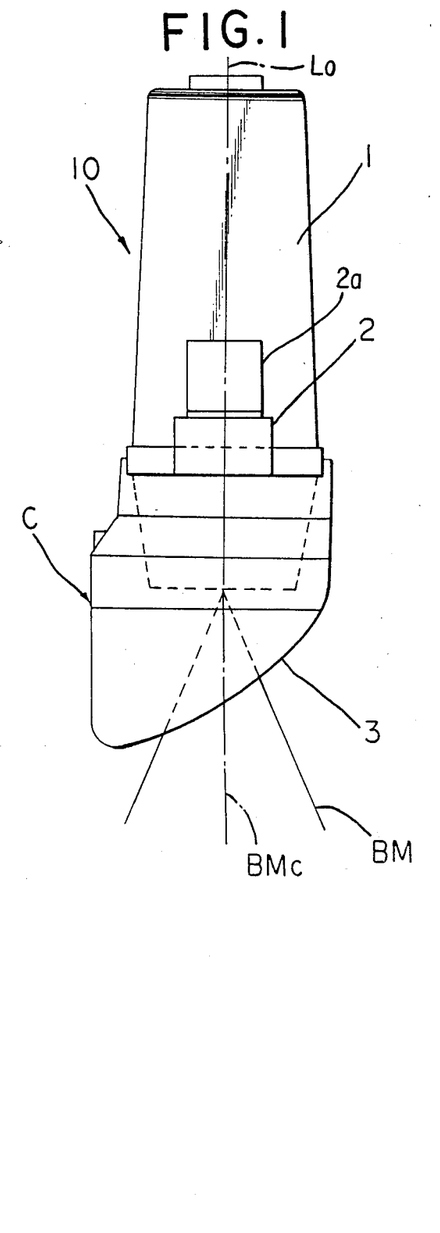
FIG. 1 is a front elevational view of an ultrasonic probe device according to an embodiment of the present invention.
Figure 2:
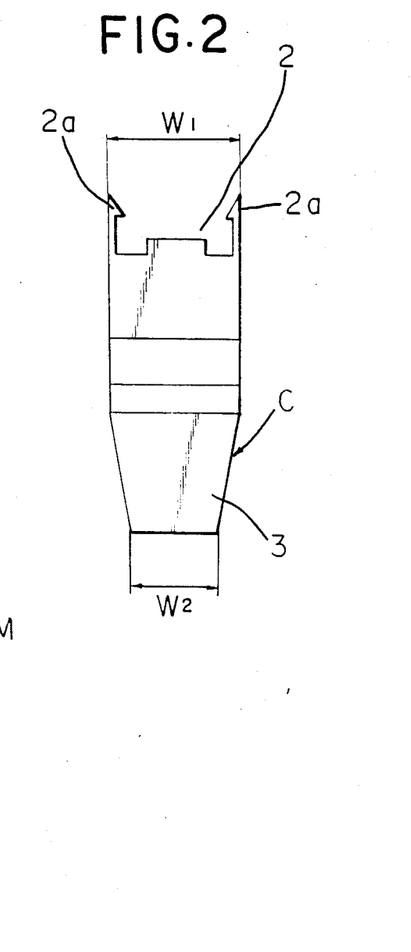
FIG. 2 is a side elevational view of an ultrasonic coupler of the ultrasonic probe device shown in FIG. 1.

An ultrasonic probe device 10 shown in FIG. 1 comprises an ultrasonic probe 1 for transmitting ultrasonic waves and receiving ultrasonic echoes and an ultrasonic coupler C mounted on the ultrasonic probe 1. The ultrasonic coupler C has a mount 2 composed of a pair of spaced hooks 2a (FIG. 2). The ultrasonic coupler C can be mounted on the ultrasonic probe 1 by snapping the hooks 2a into locking engagement with the opposite side walls of the distal end of the ultrasonic probe 1.

Figure 3:
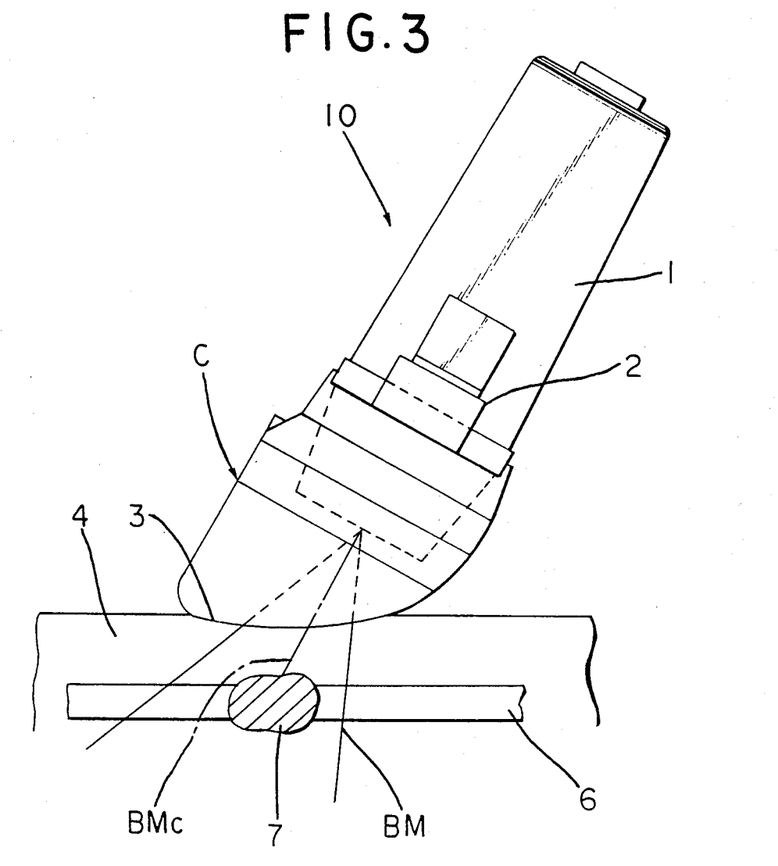
FIG. 3 is a front elevational view showing the manner in which the ultrasonic probe device of FIG. 1 is used.

The ultrasonic coupler C has a contacting surface 3 inclined at an angle (for example, 60°) to the central line BMc of an ultrasonic beam BM emitted from the ultrasonic probe 1, the contacting surface 3 having a convex curved shape of a certain curvature. As shown in FIGS. 1 and 3, for example, ultrasonic beam BM expands in a planar form toward a body to be examined. Ultrasonic beam BM thus defines a scanning plane or scanning surface.

Figure 4:
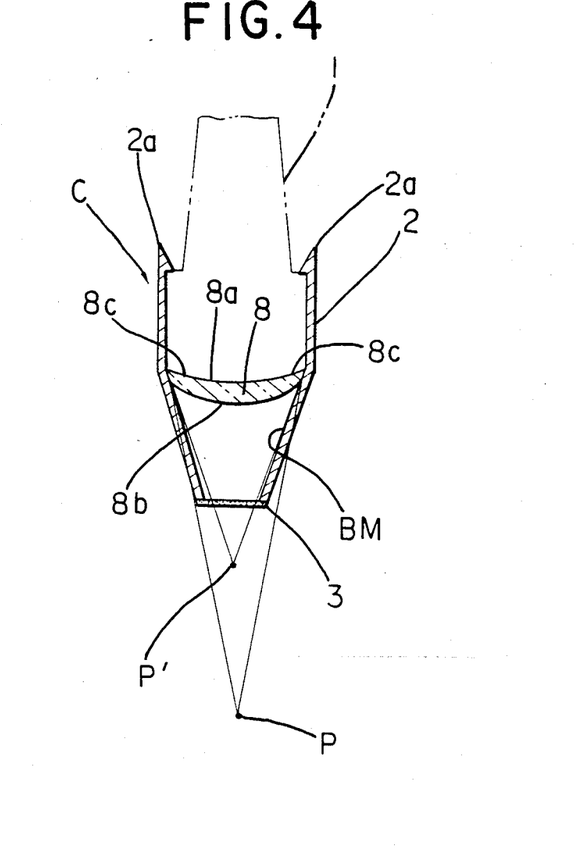
FIG. 4 is a cross-sectional view of the ultrasonic coupler of FIG. 2.

As shown in FIG. 2, the mount 2 of the ultrasonic coupler C has a width W1, whereas the contacting surface 3 thereof has a width W2 smaller than the width W1, the widths W1, W2 being across a direction in which the ultrasonic probe 1 is moved to scan an object. As shown in FIG. 4, therefore, the ultrasonic coupler C has a cross-sectional shape progressively narrower or tapered from the mount 2 toward the contacting surface 3 along the ultrasonic beam BM emitted from the ultrasonic probe 1.

The ultrasonic coupler C has an outer shell or housing made of plastics, for example, and contains an acoustic medium such as water or other liquid. Alternatively, the ultrasonic coupler C may comprise a colloidal solid substance and its holder. Where water or other liquid is housed as an acoustic medium, the contacting surface 3 is composed of a film of silicone rubber.

As illustrated in FIG. 4, the ultrasonic coupler C houses an acoustic lens 8 mounted in the mount 2. The acoustic lens 8 has an upper surface 8a having the same radius of curvature as that of an acoustic lens in the ultrasonic probe 1, and a lower surface 8b having a smaller radius of curvature. The focus point P' of the lens 8 is thus closer toward the ultrasonic coupler C than the focus point P of the ultrasonic probe 1 itself. An appropriate acoustic couplant such as jelly for example is preferably interposed between the ultrasonic probe 1 and the acoustic lens 8.

Operation and advantages of the ultrasonic probe device 10 thus constructed will be described below.

As shown in FIG. 3, the ultrasonic probe device 10 is used to detect Doppler information on a carotid artery 6, for example, running parallel to the surface of a body M being examined. The central line BMc of an ultrasonic beam BM emitted from the ultrasonic probe 1 is inclined with respect to a target region 7 of the carotid artery 6. The overall configuration of the ultrasonic coupler C is asymmetrical with respect to the central axis BMc of the ultrasonic beam BM. Therefore, the Doppler shift frequency fd can be determined since the angle α based on the Doppler effect is not 90°. Furthermore, reflected echoes from the target region 7 are not subject to multiple reflections in the ultrasonic coupler C. As a result, Doppler information on the target region 7 can accurately be detected.

In general carotid artery diagnosis, it is important to obtain information on an area where internal and external carotid arteries are branched from a common carotid artery and information on the internal carotid artery. The positions of such an area and the internal carotid artery vary from body to body. In some cases, they are positioned in a considerably higher portion, i.e., in the jaw, and the ultrasonic beam BM must be radiated obliquely upwardly from the neck. Since the contacting surface 3 of the ultrasonic coupler C of the invention is slanted, it easily allows radiation of the ultrasonic beam obliquely upwardly.

Since the contacting surface 3 to be held against the body surface 4 is of a convex curved shape of certain curvature, the transmittivity for the ultrasonic beam BM at the contacting surface 3 is high, and reflected echoes are weak, resulting in reduced multiple reflections on the sides of the ultrasonic coupler C. Because the width W2 of the contacting surface 3 is smaller than the width W1 of the probe mount 2, the contacting surface 3 can well be held in contact with the body surface 4. More specifically, the smaller width W2 of the contacting surface 3 permits the latter to move on the body surface 4 in the direction of the arrow E (FIG. 5) with reduced friction. In addition, when the ultrasonic probe device 1 is pivoted about a point on the body surface 4, as shown in FIG. 6, the ultrasonic probe device 1 can smoothly get into the body for sufficient contact with the body surface.

The acoustic lens 8 is mounted in the mount 2, and the radius of curvature of the upper surface 8a of the acoustic lens 8 is the same as that of the acoustic lens in the ultrasonic probe 1 whereas the radius of curvature of the lower surface 8a of the acoustic lens 8 is smaller, so that the focus point P' of the acoustic lens 8 is closer toward the ultrasonic coupler C than the focus point P of the ultrasonic probe device 1 itself. This enables the ultrasonic probe device 1 to observe a superficial organ such as a thyroid gland or a carotid artery with a high image quality and in a wide range of view.

FIGS. 7 through 10 show an ultrasonic probe device according to another embodiment of the present invention. The ultrasonic probe device, generally denoted at 10', comprises an ultrasonic probe 11 for transmitting ultrasonic waves and receiving ultrasonic echoes and an ultrasonic coupler C mounted on the ultrasonic probe 11.

Figure 7:
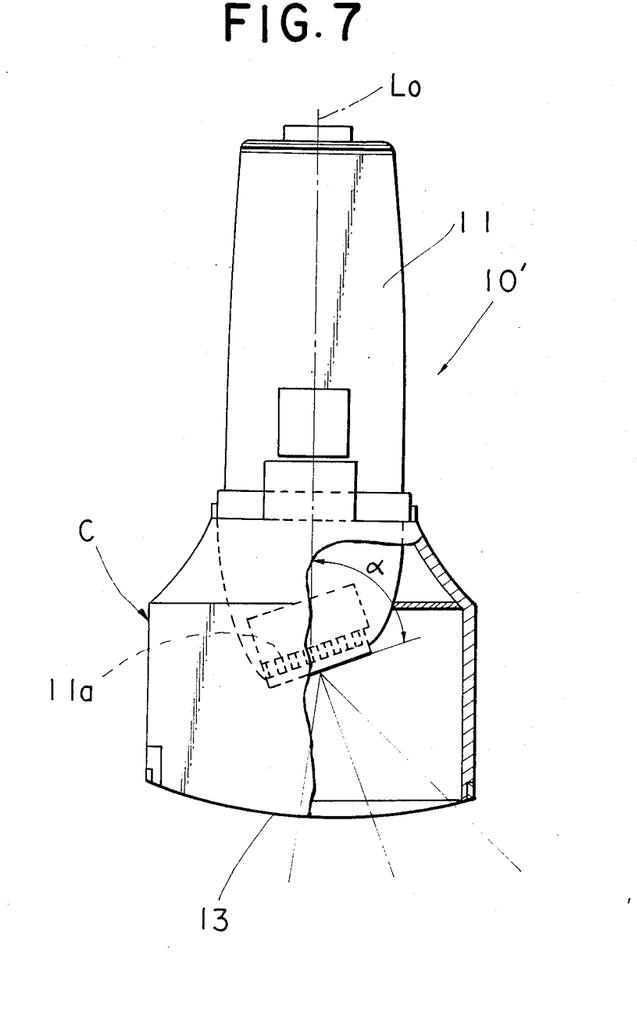
FIG. 7 is a front elevational view, partly cut away, of an ultrasonic probe device according to another embodiment of the present invention.

The ultrasonic probe 11 has an arrangement of a vibrator array 11a disposed in one end thereof positioned in the ultrasonic coupler C, the vibrator array 11a being inclined at α (for example, 60°) to the central axis Lo of the ultrasonic probe 11.

Figure 8:
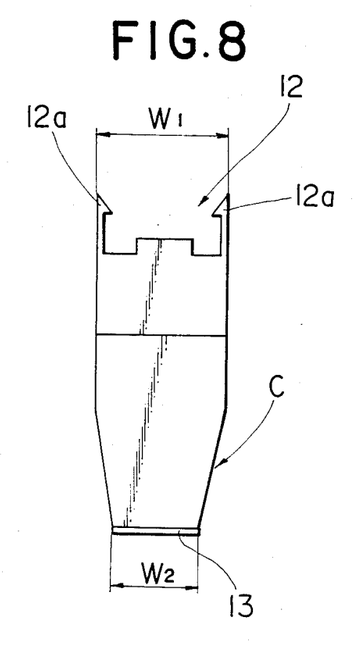
FIG. 8 is a side elevational view of an ultrasonic coupler of the ultrasonic probe device shown in FIG. 7.

As shown in FIG. 8, the ultrasonic coupler C includes a mount 12 composed of a pair of spaced hooks 12a. The ultrasonic coupler C can be mounted on the ultrasonic probe 11 by snapping the hooks 12a into locking engagement with the opposite side walls of the distal end of the ultrasonic probe 11.

The ultrasonic couple C has a contacting surface 13 having a convex curved shape of a certain curvature.

Figure 9:
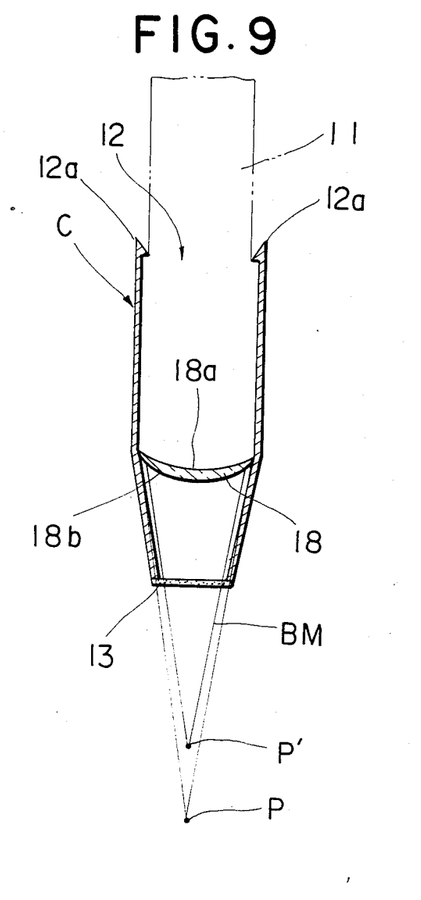
FIG. 9 is a cross-sectional view of the ultrasonic coupler shown in FIG. 8.

As shown in FIG. 8, the mount 12 of the ultrasonic coupler C has has a width W1, whereas the contacting surface 13 thereof has a width W2 smaller than the width W1, the widths W1, W2 being across a direction in which the ultrasonic probe 11 is moved to scan an object. As shown in FIGS. 8 and 9, therefore, the ultrasonic coupler C has a cross-sectional shape progressively narrower or tapered from the mount 12 toward the contacting surface 13 along the ultrasonic beam BM emitted from the ultrasonic probe 11.

The ultrasonic coupler C has an outer shell or housing made of plastics, for example, and contains an acoustic medium such as water or other liquid. Alternatively, the ultrasonic coupler C may comprise a colloidal solid substance and its holder. Where water or other liquid is housed as an acoustic medium, the contacting surface 13 is composed of a film of silicone rubber.

As illustrated in FIG. 9, the ultrasonic coupler C houses an acoustic lens 18 mounted in the mount 12. The acoustic lens 18 has an upper surface 18a having the same radius of curvature as that of an acoustic lens in the ultrasonic probe 11, and a lower surface 18b having a smaller radius of curvature. The focus point P' of the lens 18 is thus closer toward the ultrasonic coupler C than the focus point P of the ultrasonic probe 11 itself. An appropriate acoustic couplant such as jelly for example is preferably interposed between the ultrasonic probe 11 and the acoustic lens 18.

Operation and advantages of the ultrasonic probe device 10' thus constructed will be described below.

Figure 10:
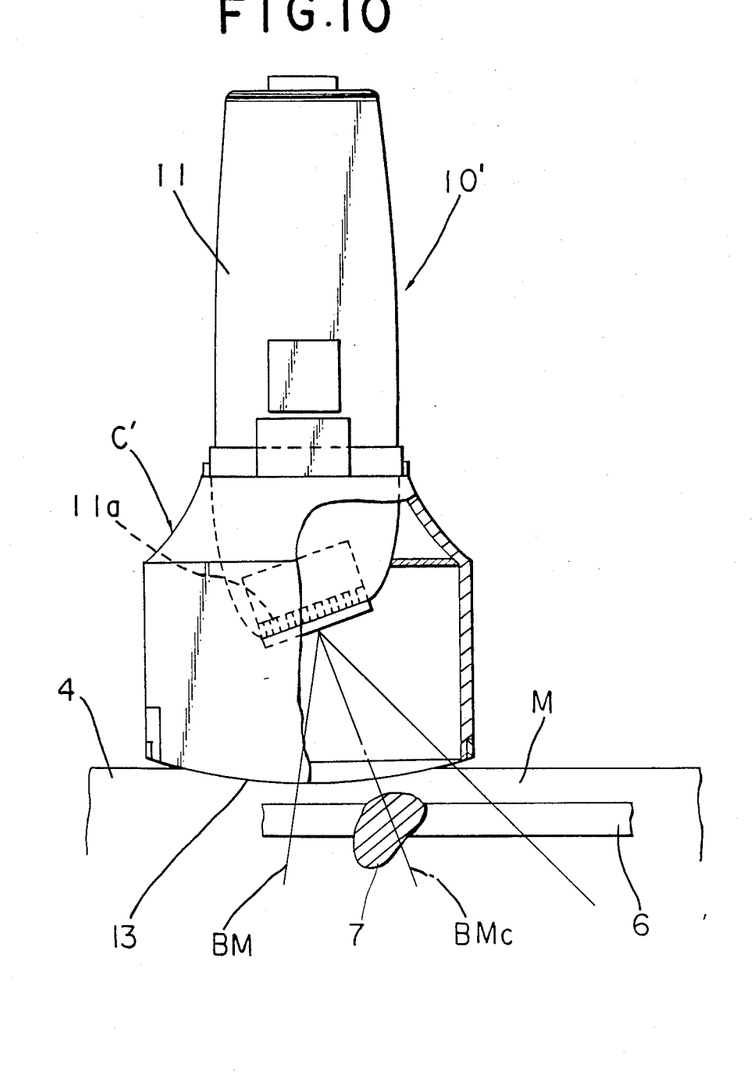
FIG. 10 is a front elevational view, partly cut away, showing the manner in which the ultrasonic probe device shown in FIG. 7 is used.

As shown in FIG. 10, the ultrasonic probe device 10' is used to detect Doppler information on a carotid artery 6, for example, running parallel to the surface of a body M being examined. The central line BMc of an ultrasonic beam BM emitted from the ultrasonic probe 11 is inclined with respect to a target region 7 of the carotid artery 6. Therefore, the Doppler shift frequency fd can be determined since the angle $\alpha$ based on the Doppler effect is not 90°. Furthermore, reflected echoes from the target region 7 are not subject to multiple reflections in the ultrasonic coupler C. As a result, Doppler information on the target region 7 can accurately be detected.

In general carotid artery diagnosis, it is important to obtain information on an area where internal and external carotid arteries are branched from a common carotid artery and information on the internal carotid artery. The positions of such an area and the internal carotid artery vary from body to body. In some cases, they are positioned in a consierably higher portion, i.e., in the jaw, and the ultrasonic beam BM must be radiated obliquely upwardly from the neck. Since the vibrator array 11a of the ultrasonic coupler C of the invention is slanted, it easily allows radiation of the ultrasonic beam obliquely upwardly.

Since the contacting surface 13 to be held against the body surface 4 is of a convex curved shape of certain curvature, the transmittivity for the ultrasonic beam BM at the contacting surface 13 is high, and reflected echoes are weak, resulting in reduced multiple reflections on the sides of the ultrasonic coupler C. The contacting surface 13 can be kept in good contact with the body surface 4.

Figure 5:
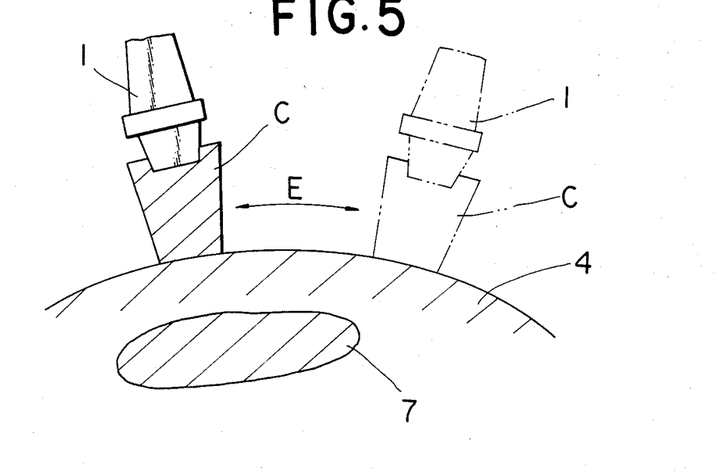
FIGS. 5 and 6 are cross-sectional views explaining operation of the ultrasonic probe device of FIG. 1.
Figure 6:
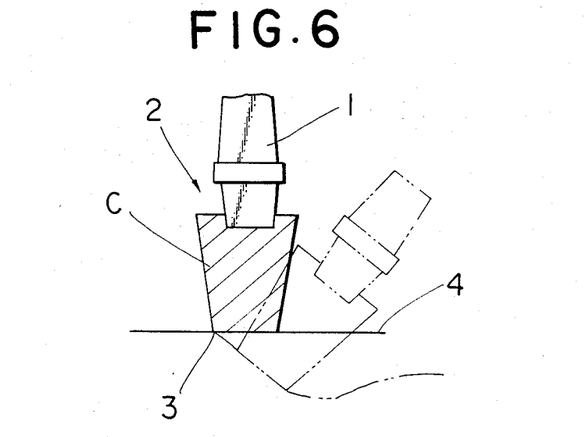
Figure 11:
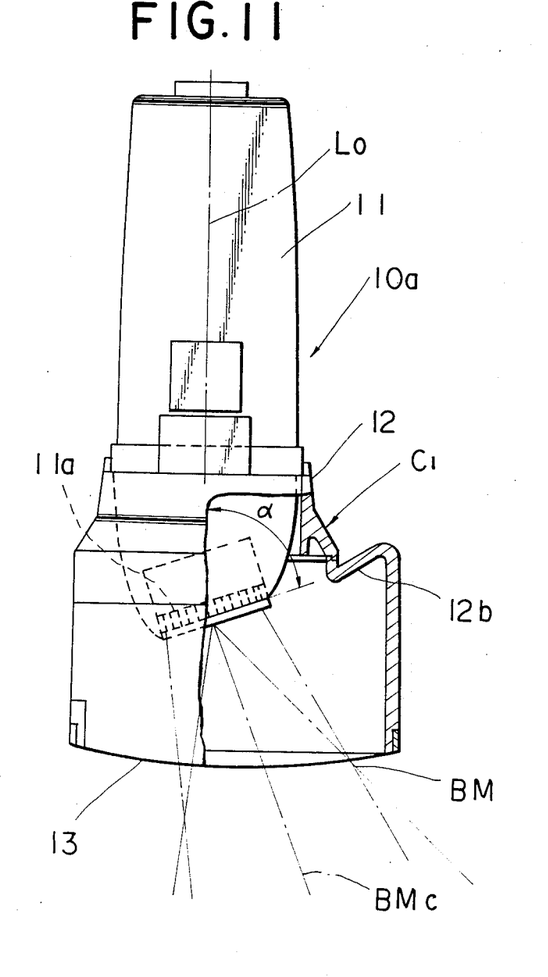
FIG. 11 is a front elevational view, partly cut away, of an ultrasonic probe device according to a modification of the present invention.

FIG. 11 shows a modification of the embodiment shown in FIG. 5. An ultrasonic probe device 10a shown in FIG. 11 differs from the ultrasonic probe device of FIG. 5 in that an ultrasonic coupler C1 has an inclined surface 12b slanted at the same angle as the angle of inclination of the vibrator array 11a of the ultrasonic probe 11.

Therefore, the distance between the inclined surface 12b of the ultrasonic coupler C1 and the contacting surface 13 is progressively greater in a direction from an end close to the vibrator array 11a toward the opposite remote end.

The ultrasonic probe device 10a has the following additional advantages: A portion of the ultrasonic beam BM reflected from the surface 4 of the body M being examined reaches the inclined surface 12b and is reflected thereby laterally so that the ultrasonic echo will not remain in the plane in which the ultrasonic beam is scanned. This greatly contributes to removal of unwanted artifact. The inclined surface 12b is also effective as an air bubble trap for trapping air bubbles produced in the water contained in the ultrasonic coupler C1.

With the embodiments shown in FIGS. 7 and 11, the vibrator array 11a of the ultrasonic probe 11 which is inclined with respect to the central axis of the ultrasonic probe 11 allows accurate detection of Doppler information on the central area of a target region.

In each of the above embodiments, the ultrasonic coupler may be housed in the ultrasonic probe so that the ultrasonic probe device is of a unitary structure.

Although certain preferred embodiments have been shown and described, it should be understood that many changes and modifications may be made therein without departing from the scope of the appended claims.

What is claimed is:

1. An ultrasonic probe device comprising:
an ultrasonic probe for transmitting ultrasonic wave beams toward a target region in a body under examination and scanning it in a planar form to form a scanning plane, said probe having a central axis in said scanning plane substantially colinear with a central line of said ultrasonic beams in said scanning plane; and
an ultrasonic coupler mounted on said ultrasonic probe and having a contact surface for contacting a surface of the body under examination;
wherein said contact surface defines a convex curved surface in said scanning plane, and wherein a line tangent to said convex curved surface at an intersection of said central line and said convex curved surface forms an oblique angle with respect to said central axis of said ultrasonic probe, said contact surface crossing at a right angle with said scanning plane.

2. An ultrasonic probe device according to claim 1, wherein said ultrasonic coupler contains an acoustic medium comprising a fluid.

3. An ultrasonic probe device according to claim 1, wherein said ultrasonic coupler comprises a colloidal substance and a holder thereof.

4. An ultrasonic probe device according to claim 1, wherein said ultrasonic coupler has a portion near said ultrasonic probe, said portion being inclined at substantially the same angle as said oblique angle.

5. An ultrasonic probe device according to claim 1, wherein said ultrasonic coupler is detachably mounted on said ultrasonic probe.

6. An ultrasonic probe device according to claim 1, wherein said ultrasonic coupler is housed in said ultrasonic probe.

* * * * *